(12) United States Patent
Johns et al.

(10) Patent No.: US 11,963,775 B2
(45) Date of Patent: Apr. 23, 2024

(54) MEDICAL SYSTEMS AND METHODS FOR DETECTING CHANGES IN ELECTROPHYSIOLOGICAL EVOKED POTENTIALS

(71) Applicant: SafeOp Surgical, Inc., Hunt Valley, MD (US)

(72) Inventors: Gregg Johns, Toronto (CA); Richard Arthur O'Brien, Westminster, MD (US); Robert Snow, Phoenix, MD (US)

(73) Assignee: SAFEOP SURGICAL, INC., Hunt Valley, MD (US)

( * ) Notice: Subject to any disclaimer, the term of this patent is extended or adjusted under 35 U.S.C. 154(b) by 0 days.

(21) Appl. No.: 15/927,921

(22) Filed: Mar. 21, 2018

(65) Prior Publication Data

US 2018/0310849 A1 Nov. 1, 2018

Related U.S. Application Data

(60) Provisional application No. 62/475,097, filed on Mar. 22, 2017.

(51) Int. Cl.
*A61B 5/24* (2021.01)
*A61B 5/00* (2006.01)
(Continued)

(52) U.S. Cl.
CPC .............. *A61B 5/24* (2021.01); *A61B 5/316* (2021.01); *A61B 5/7217* (2013.01); *A61B 5/746* (2013.01);
(Continued)

(58) Field of Classification Search
CPC ............ A61B 5/04001; A61B 5/04018; A61B 5/7217; A61B 5/746; A61B 2505/05;
(Continued)

(56) References Cited

U.S. PATENT DOCUMENTS

| 4,161,945 A | 7/1979 | Grossman |
| 4,305,402 A | 12/1981 | Katims |

(Continued)

FOREIGN PATENT DOCUMENTS

| CA | 101401724 A | 4/2009 |
| CN | 1538823 A | 10/2004 |

(Continued)

OTHER PUBLICATIONS

A. Mojsilovic, M.V. Popovic, D.M. Rackov "On the Selection of an Optimal Wavelet Basis for Texture Characterization" IEEE Trans. Image Process., 9 (2000), pp. 2043-2050. (hereinafter—Mojsiliovic) (Year: 2000).*

(Continued)

*Primary Examiner* — Yi-Shan Yang
*Assistant Examiner* — Joseph A Tombers
(74) *Attorney, Agent, or Firm* — Dentons Durham Jones Pinegar; Sarah W. Matthews

(57) ABSTRACT

A medical method of automatically improving signals received from a patient's physiological system can include delivering stimulation signals to a nerve pathway of a patient with electrical pulses via electrodes placed over the nerve pathway to generate a plurality of resultant electrical waveforms (EPs) based on a plurality of electrophysiological responses (ERs); recording the plurality of resultant EPs; generating an ensemble average waveform (EA), the generating comprising averaging a subset of the plurality of ERs; and denoising the EA, the denoising comprising applying a wavelet transform to the EA.

17 Claims, 5 Drawing Sheets

(51) Int. Cl.
*A61B 5/021* (2006.01)
*A61B 5/316* (2021.01)
*A61N 1/04* (2006.01)
*A61N 1/36* (2006.01)

(52) U.S. Cl.
CPC ............ *A61B 5/021* (2013.01); *A61B 5/4821* (2013.01); *A61B 2505/05* (2013.01); *A61N 1/0456* (2013.01); *A61N 1/36014* (2013.01)

(58) Field of Classification Search
CPC .... A61B 5/021; A61B 5/4821; A61N 1/0456; A61N 1/36014
See application file for complete search history.

(56) References Cited

U.S. PATENT DOCUMENTS

| | | | |
|---|---|---|---|
| 4,863,265 A | 9/1989 | Flower et al. | |
| 4,934,377 A | 6/1990 | Bova et al. | |
| 5,284,154 A | 2/1994 | Raymond et al. | |
| 5,313,956 A | 5/1994 | Knutsson et al. | |
| 5,662,105 A | 9/1997 | Tien | |
| 5,797,854 A | 8/1998 | Hedgecock | |
| 5,825,936 A | 10/1998 | Clarke et al. | |
| 5,827,195 A * | 10/1998 | Lander ................. | A61B 5/7203 600/509 |
| 5,916,179 A | 6/1999 | Sharrock | |
| 6,067,467 A | 5/2000 | John | |
| 6,304,772 B1 | 10/2001 | Taha et al. | |
| 6,391,024 B1 | 5/2002 | Sun et al. | |
| 6,535,767 B1 | 3/2003 | Kronberg | |
| 6,556,861 B1 | 4/2003 | Prichep | |
| 6,634,043 B2 | 10/2003 | Lamb et al. | |
| 6,725,086 B2 | 4/2004 | Marinello | |
| 6,985,833 B2 | 1/2006 | Shambroom et al. | |
| 7,174,206 B2 | 2/2007 | Frei et al. | |
| 7,216,001 B2 | 5/2007 | Hacker et al. | |
| 7,234,180 B2 | 6/2007 | Horton et al. | |
| 7,512,439 B1 | 3/2009 | Farazi | |
| 7,522,953 B2 | 4/2009 | Kaula et al. | |
| 7,620,453 B1 | 11/2009 | Propato et al. | |
| 7,628,757 B1 | 12/2009 | Koh | |
| 7,628,761 B2 | 12/2009 | Gozani et al. | |
| 7,806,862 B2 | 10/2010 | Molnar | |
| 7,904,160 B2 | 3/2011 | Brodnick et al. | |
| 8,055,349 B2 | 11/2011 | Gharib et al. | |
| 8,108,039 B2 | 1/2012 | Saliga et al. | |
| 8,255,045 B2 | 8/2012 | Gharib et al. | |
| 8,386,025 B2 | 2/2013 | Hoppe | |
| 8,515,530 B2 | 8/2013 | Warner et al. | |
| 8,538,512 B1 | 9/2013 | Bibian et al. | |
| 8,538,539 B2 | 9/2013 | Gharib et al. | |
| 8,568,331 B2 | 10/2013 | Bertagnoli et al. | |
| 8,591,431 B2 | 11/2013 | Calancie et al. | |
| 8,731,654 B2 | 5/2014 | Johnson et al. | |
| 8,740,783 B2 | 6/2014 | Gharib et al. | |
| 8,903,487 B1 | 12/2014 | Fischell et al. | |
| 8,965,520 B2 | 2/2015 | Botros et al. | |
| 8,989,866 B2 | 3/2015 | Gharib et al. | |
| 9,084,551 B2 | 7/2015 | Brunnett et al. | |
| 9,095,266 B1 * | 8/2015 | Fu ........................ | G16H 50/20 |
| 9,211,074 B2 | 12/2015 | Johnson et al. | |
| 9,332,918 B1 | 5/2016 | Buckley et al. | |
| 9,579,037 B2 | 2/2017 | Brunnett et al. | |
| 9,585,618 B2 | 3/2017 | Leschinsky | |
| 9,681,880 B2 | 6/2017 | Neubardt et al. | |
| 9,700,228 B2 | 7/2017 | Gharib et al. | |
| 9,743,853 B2 | 8/2017 | Kelleher | |
| 9,743,884 B2 | 8/2017 | Rasmussen | |
| 9,744,356 B2 | 8/2017 | Botros et al. | |
| 10,342,443 B2 | 7/2019 | Johnson et al. | |
| 10,376,167 B2 | 8/2019 | Mahon et al. | |
| 10,391,012 B2 | 8/2019 | Stashuk et al. | |
| 11,083,387 B2 | 8/2021 | Mahon et al. | |
| 11,197,640 B2 | 12/2021 | Johns et al. | |
| 11,684,533 B2 | 6/2023 | Stashuk et al. | |
| 2002/0042563 A1 | 4/2002 | Becerra et al. | |
| 2002/0183605 A1 | 12/2002 | Devlin et al. | |
| 2003/0052775 A1 | 3/2003 | Shambroom et al. | |
| 2003/0083719 A1 | 5/2003 | Shankar et al. | |
| 2003/0125777 A1 | 7/2003 | Ding et al. | |
| 2003/0176799 A1 | 9/2003 | Beatty et al. | |
| 2004/0010203 A1 * | 1/2004 | Bibian ................... | A61B 5/726 600/544 |
| 2004/0010303 A1 | 1/2004 | Bolea | |
| 2004/0122482 A1 | 6/2004 | Tung et al. | |
| 2005/0075578 A1 | 4/2005 | Gharib et al. | |
| 2005/0085866 A1 | 4/2005 | Tehrani | |
| 2005/0101878 A1 | 5/2005 | Daly et al. | |
| 2005/0119711 A1 | 6/2005 | Cho et al. | |
| 2005/0228306 A1 | 10/2005 | Kurtz | |
| 2005/0228654 A1 | 10/2005 | Prieto et al. | |
| 2005/0261559 A1 | 11/2005 | Mumford et al. | |
| 2006/0025702 A1 | 2/2006 | Sterrantino et al. | |
| 2006/0052845 A1 | 3/2006 | Zanella | |
| 2006/0173510 A1 | 8/2006 | Besio et al. | |
| 2006/0178593 A1 | 8/2006 | Neubardt et al. | |
| 2006/0241562 A1 | 10/2006 | John et al. | |
| 2006/0276704 A1 | 12/2006 | Mcginnis et al. | |
| 2007/0016097 A1 | 1/2007 | Farquhar et al. | |
| 2007/0135722 A1 | 6/2007 | Lin | |
| 2007/0192960 A1 | 8/2007 | Jackson | |
| 2007/0225674 A1 | 9/2007 | Molnar et al. | |
| 2007/0282217 A1 | 12/2007 | McGinnis et al. | |
| 2008/0033511 A1 | 2/2008 | Dobak | |
| 2008/0051844 A1 | 2/2008 | Brodnick et al. | |
| 2008/0167574 A1 | 7/2008 | Farquhar | |
| 2008/0221473 A1 | 9/2008 | Calancie et al. | |
| 2008/0269835 A1 | 10/2008 | Carlson et al. | |
| 2008/0300655 A1 | 12/2008 | Cholette | |
| 2009/0033486 A1 | 2/2009 | Costantino | |
| 2009/0048531 A1 | 2/2009 | Mcginnis et al. | |
| 2009/0054758 A1 | 2/2009 | Dunseath | |
| 2009/0054804 A1 | 2/2009 | Gharib et al. | |
| 2009/0069027 A1 | 3/2009 | Brock et al. | |
| 2009/0124869 A1 | 5/2009 | Hu et al. | |
| 2009/0143693 A1 | 6/2009 | Ye et al. | |
| 2009/0149148 A1 * | 6/2009 | Kurtz ................. | G06K 9/00536 455/307 |
| 2009/0177112 A1 | 7/2009 | Gharib et al. | |
| 2009/0247893 A1 * | 10/2009 | Lapinlampi ............ | A61B 5/369 600/546 |
| 2010/0010367 A1 | 1/2010 | Foley et al. | |
| 2010/0036211 A1 | 2/2010 | La Rue et al. | |
| 2010/0042012 A1 | 2/2010 | Alhussiny | |
| 2010/0130834 A1 | 5/2010 | Mertio-Oja et al. | |
| 2010/0156376 A1 | 6/2010 | Fu et al. | |
| 2010/0198099 A1 | 8/2010 | Murphy et al. | |
| 2010/0274144 A1 | 10/2010 | Hu et al. | |
| 2010/0312124 A1 | 12/2010 | Johnson et al. | |
| 2010/0317989 A1 | 12/2010 | Gharib et al. | |
| 2011/0054346 A1 | 3/2011 | Hausman et al. | |
| 2011/0105939 A1 | 5/2011 | Yong et al. | |
| 2011/0224570 A1 | 9/2011 | Causevic | |
| 2011/0224988 A1 | 9/2011 | Mahajan et al. | |
| 2011/0230785 A1 | 9/2011 | Higgins et al. | |
| 2011/0279676 A1 | 11/2011 | Terada et al. | |
| 2011/0295142 A1 | 12/2011 | Chakravarthy et al. | |
| 2012/0065536 A1 | 3/2012 | Causevic et al. | |
| 2012/0095360 A1 | 4/2012 | Runney et al. | |
| 2012/0136276 A1 | 5/2012 | Johnson et al. | |
| 2012/0150063 A1 | 6/2012 | Rea | |
| 2012/0165690 A1 | 6/2012 | Chen et al. | |
| 2012/0197153 A1 | 8/2012 | Kraus et al. | |
| 2012/0313757 A1 | 12/2012 | Volpi et al. | |
| 2013/0024524 A1 | 1/2013 | Graff et al. | |
| 2013/0035606 A1 | 2/2013 | Wichner | |
| 2013/0190599 A1 | 7/2013 | Wyeth et al. | |
| 2013/0204156 A1 | 8/2013 | Hampton et al. | |
| 2013/0245424 A1 | 9/2013 | Decharms | |
| 2013/0245722 A1 | 9/2013 | Ternes et al. | |
| 2014/0020178 A1 | 1/2014 | Stashuk et al. | |
| 2014/0121555 A1 | 5/2014 | Scott et al. | |
| 2014/0148725 A1 | 5/2014 | Cadwell | |

(56) References Cited

U.S. PATENT DOCUMENTS

| | | |
|---|---|---|
| 2014/0275926 A1 | 9/2014 | Scott |
| 2014/0276195 A1 | 9/2014 | Papay et al. |
| 2014/0288389 A1 | 9/2014 | Gharib et al. |
| 2014/0324118 A1 | 10/2014 | Simon et al. |
| 2015/0061758 A1 | 3/2015 | Hsu |
| 2015/0088030 A1 | 3/2015 | Taylor |
| 2015/0148683 A1 | 5/2015 | Hermanne |
| 2015/0208934 A1 | 7/2015 | Sztrubel et al. |
| 2015/0257700 A1 | 9/2015 | Fu |
| 2015/0313512 A1 | 11/2015 | Hausman et al. |
| 2016/0106994 A1 | 4/2016 | Crosby et al. |
| 2016/0113587 A1 | 4/2016 | Kothe et al. |
| 2016/0128620 A1 | 5/2016 | Iriki et al. |
| 2016/0213268 A1 | 7/2016 | Kim et al. |
| 2016/0228018 A1 | 8/2016 | Mahon et al. |
| 2016/0270679 A1* | 9/2016 | Mahon .................. A61N 1/0456 |
| 2017/0347955 A1 | 12/2017 | Rasmussen |
| 2018/0078210 A1 | 3/2018 | Snow et al. |
| 2018/0140843 A1 | 5/2018 | Kent et al. |
| 2018/0310849 A1 | 11/2018 | Johns et al. |
| 2018/0360336 A1 | 12/2018 | O'Brien et al. |
| 2020/0315478 A1 | 10/2020 | Mahon et al. |
| 2022/0096022 A1 | 3/2022 | Johns et al. |
| 2022/0287619 A1 | 9/2022 | Cleveland et al. |

FOREIGN PATENT DOCUMENTS

| | | |
|---|---|---|
| CN | 101137332 A | 3/2008 |
| CN | 101309419 A | 11/2008 |
| CN | 201185940 Y | 1/2009 |
| CN | 102361590 A | 2/2012 |
| CN | 102368951 A | 3/2012 |
| CN | 102481107 A | 5/2012 |
| CN | 102594472 A | 7/2012 |
| CN | 102824170 A | 12/2012 |
| CN | 102883775 A | 1/2013 |
| CN | 104411234 A | 3/2015 |
| CN | 104994782 A | 10/2015 |
| CN | 105873506 A | 8/2016 |
| CN | 105902262 A | 8/2016 |
| JP | S51154986 U | 12/1976 |
| JP | S5922106 A | 7/1982 |
| JP | S59193403 A | 4/1983 |
| JP | H04253843 A | 12/1991 |
| JP | H06508288 A | 9/1994 |
| JP | H06277189 A | 10/1994 |
| JP | H1176185 A | 3/1999 |
| JP | 2003131668 A | 5/2003 |
| JP | 2004517669 A | 6/2004 |
| JP | 2005073223 A | 3/2005 |
| JP | 2007185326 A | 7/2007 |
| JP | 2009502424 A | 1/2009 |
| JP | 2005519646 A | 4/2009 |
| JP | 2009071387 A | 4/2009 |
| JP | 2009118969 A | 6/2009 |
| JP | 2009534159 A | 9/2009 |
| JP | 2010104586 A | 5/2010 |
| JP | 2012529344 A | 11/2012 |
| JP | 2012236007 A | 12/2012 |
| JP | 5466389 B2 | 4/2014 |
| JP | 2017502711 A | 1/2017 |
| JP | 2017502711 A1 | 1/2017 |
| WO | 2001074248 A1 | 10/2001 |
| WO | 02100267 A1 | 12/2002 |
| WO | 2003000128 A2 | 1/2003 |
| WO | 2003005887 A2 | 1/2003 |
| WO | 2006072050 A2 | 7/2006 |
| WO | 2006084193 A2 | 8/2006 |
| WO | 2007016149 A2 | 2/2007 |
| WO | 2010144200 A1 | 12/2010 |
| WO | 2011045936 A1 | 4/2011 |
| WO | 2013166157 A1 | 11/2013 |
| WO | 2015048822 A1 | 5/2015 |
| WO | 2015069949 A1 | 5/2015 |
| WO | 2016179191 A1 | 11/2016 |
| WO | 2018232365 A1 | 12/2018 |
| WO | 2022192569 A1 | 9/2022 |

OTHER PUBLICATIONS

Extended European Search Report dated Dec. 3, 2020, for EP Patent Application 18771706.1, 8 pages.

Iyer, D. et al. (Mar. 2007, e-published Dec. 26, 2006). "Single-trial evoked potential estimation: comparison between independent component analysis and wavelet denoising," *Clin Neurophysiol* 118(3):495-504.

Patel, R. et al. (Apr. 1, 2017). "Effective Extraction of Visual Event-Related Pattern by Combining Template Matching with Ensemble Empirical Mode Decomposition," *IEEE Sensors Journal* 17(7):2146-2153.

Zou, L. et al. (Jun. 6, 2010). "Estimation of Event Related Potentials Using Wavelet Denoising Based Method," *Advances in Neural Networks* 400-407.

"NeuroStream—Intraoperative Monitoring Document Management" [online][retrieved Apr. 21, 2010). Retrieved from the Internet at <http://www.neurostream.us/solutionsonlineDoc.iso?nav=1>.

"NeuroStream—Intraoperative Monitoring Interpreting Physician Access" [online][retrieved Apr. 21, 2010). Retrieved from the Internet at HYPERLINK "http://www.neurostream.us/solutionstelemedicine.iso?nav=1".

"NeuroStream—IOM and Neurophysiological Monitoring Software" [online][retrieved Apr. 21, 2010). Retrieved from the Internet at HYPERLINK "http://www.neurostream.us/solutionscaseExecution.iso?nav=1".

"NeuroStream—Software for Intraoperative Monitoring Scheduling" [online][retrieved Apr. 21, 2010). Retrieved from the Internet at HYPERLINK h http://www.neurostream.us/solutionsschedulina.iso?nav= 1.

AMSCO 3085 SP Surgical Table Sales Brochure, STERIS Corporation; Apr. 2006, 16 pages.

Baumann, et al., Intraoperative SSEP Detection of Ulnar Nerve Compression or Ischemia in an Obese Patient: A Unique Complication Associated With a Specialized Spinal Retraction System; Archives of Physical Medicine and Rehabilitation, vol. 81.

Ben-David, et al., Prognosis of Intraoperative Brachial Plexus Injury: A Review of 22 cases, British Journal of Anaesthesia, vol. 79, No. 4, Oct. 1997, pp. 440-445.

Bizzarri, et al., Iatrogenic Injury to the Long Thoracic Nerve: An Underestimated Cause of Morbidity After Cardiac Surgery, Texas Heart Institute Journal, vol. 28, No. 4, Jan. 2001, pp. 315-317.

Chung, Induk, et al., "Upper-limb somatosensory evoked potential monitoring in lumbosacral spine surgery: a prognostic marker for position-related ulnar nerve injury." The Spine Journal 9.4 (Apr. 2009): 287-295.

Crum, et al. "Peripheral nerve stimulation and monitoring during operative procedures." Muscles & nerve 35.2:159-170. (Year: 2007).

Crum, et al. "intraoperative peripheral nerve stimulation and recording." Handbook of Clinical Neurophysiology 8: 364-370. (Year: 2008).

Doemges, et al., "Changes in the Stretch Reflex of the Human First Dorsal Interosseous Muscle During Different Tasks," Journal of Physiology, 1992, pp. 563-573, vol. 447.

European Patent Office acting as International Searching Authority, "Search Report and Written Opinion," International Application No. PCT/US2022/019798, dated Jul. 6, 2022.

European Patent Office, "Communication Pursuant to Article 94(3) EPC," European Application No. 18771706.1, dated Jul. 4, 2023.

European Patent Office, "Extended European Search Report," European Application No. 23188630.0, dated Sep. 5, 2023.

Fishel, et al., Case Report: Postoperative Injuries of Upper Limb Nerves, The Clinical Journal of Pain, vol. 6, No. 2, Jun. 1990, pp. 128-130.

Graham, et al., Brachial Plexus Injury After Median Sternotomy, Journal of Neurology, Neurosurgery, and Psychiatry, vol. 44, Jul. 1981, pp. 621-625.

(56) References Cited

OTHER PUBLICATIONS

Hickey et al., "Intraoperative Somatosensory Evoked Potential Monitoring Predicts Peripheral Nerve Injury During Cardiac Surgery", Anesthesiology 78(1), 29-35 (1993).
Hongxuan Zhang et al., "Intraoperative Neurological Monitoring," vol. 25, No. 4, Jul. 1, 2006 (Jul. 1, 2006), pp. 39-45.
International Search Report and Written Opinion for Application No. PCT/US2014/064433, dated Apr. 4, 2015, 10 pages.
International Search Report and Written Opinion for PCT Application No. PCT/US2010/034076, dated Jul. 9, 2010, 8 pages.
International Search Report and Written Opinion, PCT/US16/30605, dated Aug. 8, 2016.
Japan Patent Office, "Office Action," Japanese Application No. 2022191709, dated Nov. 14, 2023.
Jellish, et al., Hands-Up Positioning During Asymmetric Sternal Retraction for Internal Mammary Artery Harvest: A Possible Method to Reduce Brachial Plexus Injury, Anesthesia and Analgesia, vol. 84, No. 2, Feb. 1997, pp. 260-265.
Kamel et al., "The Use of Sematosensory Evoked Potentials to Determine the Relationship Between Patient Positioning and Impending Upper Extremity Nerve Injury During Spine Surgery: A Retrospective Analysis", Anesth Analg 102(5), 1538-1542 (2006).
Labrom et al., "Clinical Usefulness of Somatosensory Evoked Potentials for Detection of Brachial Plexopathy Secondary to Malpositioning in Scoliosis Surgery", Spine 30(18), 2089-2093 (2005).
Makarov, et al., Intraoperative SSEP Monitoring During External Fixation Procedures in the Lower Extremities, Journal of Pediatric Orthopaedics, vol. 16, No. 2, Mar./Apr. 1996, pp. 155-160.
Makarov, et al., Monitoring Peripheral Nerve Function During External Fixation of Upper Extremities, Journal of Pediatric Orthopaedics, vol. 17, No. 5, Sep./Oct. 1997, pp. 663-667.
Makeig, et al., Mining event-related brain dynamics, Trends in Cognitive Sciences. vol. 8, No. 5, May 2004, pp. 204-210.
Nagda, et al., Neer Award 2005: Peripheral Nerve Function During Shoulder Arthoplasty Using Intraoperative Nerve Monitoring, Journal of Shoulder and Elbow Surgery, vol. 16, No. 3, Supplement, May-Jun. 2007, 7 pages.
Posta, Jr., et al., Neurologic Injury in the Upper Extremity After Total Hip Arthroplasty, Clinical Orthopaedics and Related Research, vol. 345, Dec. 1997, pp. 181-186.
Prielipp, et al., Ulnar Nerve Pressure: Influence of Arm Position and Relationship to Somatosensory Evoked Potentials, Anesthesiology, vol. 91, No. 2, Aug. 1999, 10 pages.
Supplemental Partial European Search Report for Application No. EP 14 86 1025, dated Jun. 16, 2017.
The International Bureau of WIPO, "International Preliminary Report on Patentability," International Application No. PCT/US2022/019798, dated Sep. 21, 2023.
Warner et al. (Dec. 1994) "Ulnar Neuropathy. Incidence, Outcome, and Risk Factors in Sedated or Anesthetized Patients", Anesthesiology, 81(6):1332-1340.
Winfree, et al., Intraoperative Positioning Nerve Injuries, Surgical Neurology, vol. 63, No. 1, Jan. 2005, pp. 5-18.
International Search Authority, "Search Report and Written Opinion," International Application No. PCT/ US/2023/029024, Dec. 15, 2023.
China National Intellectual Property Adminsitration, "Office Action," Chinese Application No. 202110429148.7, Nov. 23, 2023.

* cited by examiner

MEDICAL SYSTEMS AND METHODS FOR DETECTING CHANGES IN ELECTROPHYSIOLOGICAL EVOKED POTENTIALS

RELATED APPLICATIONS

This application claims priority to U.S. Provisional Application No. 62/475,097, filed on Mar. 22, 2017, the entirety of which is incorporated by reference herein.

This application is related to International Patent Application No. PCT/US2016/0030605 (published as International Publication WO2016/179191), filed May 3, 2016, entitled "SYSTEM, METHOD, AND COMPUTER ALGORITHM FOR MEASURING, DISPLAYING, AND ACCURATELY DETECTING CHANGES IN ELECTROPHYSIOLOGICAL EVOKED POTENTIALS," which claims the benefit of and priority to U.S. Provisional Application No. 62/156,874 filed May 4, 2015, both of which are incorporated herein by reference in their entireties.

BACKGROUND

The present invention relates generally to medical systems, instruments, apparatus and methods for improving and automatically detecting changes in evoked potentials (EPs), and more particularly to medical systems and medical methods to automatically detect changes in evoked potentials (EPs) by removing confounding noise from the signals.

Bio-electrical potentials such as Somatosensory evoked potentials (SSEP), auditory evoked potentials (AER) and/or visual evoked potentials (VER), among others are summated electrical potentials usually recorded after repeatedly stimulating a peripheral nerve or other parts of the nervous system. Monitoring patients by recording waveforms such as somatosensory evoked potentials during surgery has been shown to allow early identification of impending injury, such as a nerve injury.

Such monitoring generally requires highly trained technologists under physician supervision with sophisticated, multichannel amplifier and display equipment. Unfortunately, such personnel and equipment are limited in their availability, require pre-booking, and are costly. In addition, such monitoring is fraught with difficulties due to the small size of potentials and large amounts of ongoing noise which makes recognizing significant changes and when to alert for these changes difficult. In typical systems that are used to generate alerts automatically, substantial noise and variability can cause false alerts. In typical systems, the generated signals may be preprocessed and/or not accurate measure and/or account for noise.

Embodiments described herein relate to improved, medical systems, instruments, methods and devices for accurately detecting changes in electrophysiological evoked potentials. Improvements to existing systems include reduction in erroneous assessments of waveform changes and erroneous alerting due to signal noise. Accordingly, the improved systems, methods, and devices generate more accurate alerts. Reducing the number of erroneous alerts also creates more efficient systems, methods, and devices compared to known systems.

SUMMARY OF THE INVENTION

When seeking to accurately monitor or detect EPs, the waveforms can require acquisition at specific frequencies and averaging together to help attenuate random and cyclical noise. Even a few aberrant waveforms heavily affected by noise can markedly change the apparent amplitude (height) or latency (time of onset) of a waveform of interest when averaged together. While this is partly avoided by careful choice of stimulation frequencies and filtering of the waveforms, such methods cannot be complete as the waveforms of interest fall within the frequency range of the background noise and the cyclical background noise varies somewhat in frequency. The difficulty with analyzing and detecting changes in the waveforms lies in the wide variation in the amplitude, frequency and shape of the waveforms. These variations are caused by many factors including anesthesia and any preexisting abnormalities of the nerves, however the main cause is electrical interference from ambient electrical noise or from other devices. For example, initially placing electrodes on the patient can create a substantial amount of noise. In such situations, impedance measured by the electrodes around the time of initial placement can be higher, which can create a large amount of noise.

Typically, averaging of waveforms and both electronic and digital filters and waveform classifiers have been employed to try to attenuate noise from the signals and allow better viewing and assessment or interpretation of the waveforms. These methods typically work in three ways: by limiting recorded waveform frequency range, by rejecting periods of recordings where signals of high amplitude that contain clear artifact are present, or by extending the number of averages included in an averaged signal. Standard filters that limit the frequency range (frequency filters) of the recordings or waveform classifiers that reject raw recordings over a certain amplitude threshold (rejection threshold filters) may have difficulty removing sufficient noise or artifact from evoked potential recordings leading to inability to record accurate signals and thus result in inaccurate calculation of waveform changes. Furthermore, these methods offer only partial removal of noise and may further alter the morphology, amplitude or even presence/absence of the underlying potentials of interest making assessment/interpretation difficult and highly dependent on experience. This in turn may lead to erroneous assessments of waveform changes and erroneous alerting.

Automated alerting systems which search for significant changes in waveforms are hampered by the transient nature of electrical noise and the limitations of typical methods for removing it. Artifacts that fall in the middle of the averaged waveform of interest can change the overall morphology of the averaged waveform that is used for analysis by introducing additional phases and making an analysis of latency of the component of interest difficult. This may lead to variation of choice in the components of the waveform being analyzed that trigger an alert and result in false alerting. Otherwise, such systems may require a trained professional to continuously monitor the waveform and make assessments. Such assessments may be inaccurate and/or costly. Such assessments may be inaccurate due to human error and/or due to the displayed waveform that does not sufficiently account for noise.

Similarly, noise introduced into the signal may alter the amplitude of the averaged signal and trigger a false alert or even mask a real change in amplitude.

Certain typical methods for detecting and removing artifact from electroencephalographic signals primarily apply to continuous EEG or ECG recordings. These methods may not be applied to stimulus evoked monitoring, are related to recurrent timed artifact, and/or do not improve alerting to signal changes. Such methods are not typically applied to evoked potentials and/or coupled to improvements in automated alerting of waveform change, among other improvements.

In view of the foregoing, there is a need for methods, devices, systems, apparatuses and/or means to automatically and more fully attenuate unwanted artifact from an ongoing series of recorded evoked potential signals in real time without significantly altering the character of the signal of interest so that alerts regarding changes in the waveform are consistent and accurate. Such configurations can allow for automated calculation of the alerts, and/or more accurate automated calculation and indicating of the alerts. The result is producing alerts free of the influence of variable noise and bias, while minimizing or eliminating false negative and false positive errors. Embodiments described herein generally relate to the computer signal processing to accomplish this task. Embodiments described herein can be used in lieu of and/or improve upon expert analysis typically provided by the technologist and physician. For example, without more accurate filtering and/or denoised signals, a technologist and/or physician may not be able to accurate asses the waveform. Further, various embodiments can be used in conjunction with other equipment. For example, upon detecting a change in EPs, an operating room table can be moved. Such movement allows the patient to be automatically moved to ameliorate or avoid patient injury. Thus various embodiments extend the benefit of such equipment by automatically controlling the equipment based upon the EPs.

In some embodiments of the current subject matter, a system and/or method can identify and attenuate unwanted noise or artifact from electrophysiological Eps, resulting in improved automated alerting of waveform changes. An EP can be defined as a voltage versus time signal obtained by ensemble averaging (EA) the electrophysiological responses (ER) to repetitive stimulation of a specific sensory neural system detected using suitable electrodes. Examples of EPs are somatosensory, auditory and/or visual EPs, among other EPs. The systems and methods can be applied to every ER signal recorded after each stimulation that survives any initial frequency and amplitude rejection filtering or classification, and/or after summation of those timed signals into an EA. The systems and/or methods can then establish the presence or absence of baseline waveform of interest and calculate any subsequent changes from the baseline in subsequent EAs.

The systems can communicate with ancillary hardware and/or other systems developed to acquire the sequence of EPs and provide suitable feedback to ensure an effective clinical workflow. The systems and/or methods can provide the basis for a clinically effective application such that false positives and false negatives are minimized.

According to some implementations, an automated evoked potential analysis apparatus for improved monitoring, detecting and identifying changes to a patient's physiological system is shown and described herein.

In some aspects, a method for automatically improving a signal received from a patient's physiological system and providing a more accurate alert as to changes in the patient's physiological system is described herein.

In some aspects, an automated evoked potential analysis apparatus for improved monitoring, detecting and identifying changes to a patient's physiological system can include an input device and a computing system. The input device can obtain electrical potential data from the patient's physiological system after application of stimulation to a patient's nerve. The computing system can receive and analyze the electrical potential data. The computing system can include a processing circuit that can generate a plurality of evoked potential waveforms (EPs) based on the electrical potential data; calculate an ensemble average waveform (EA) of a subset of the plurality of EPs; apply a mathematical wavelet transform to the resultant EA; attenuate noise components from the transformed EA; and/or apply an inverse transform to the transformed EA to generate a denoised EA, among other things.

In some aspects, the computing system can calculate a change in the denoised EA relative to a previous denoised EA; and provide an alert based on the calculated change.

In some aspects, the apparatus can integrate into other devices in a surgical environment.

In some aspects, the computing system can feed information to other devices in the surgical environment that allows these devices to manually or automatically identify changes between the denoised EA and a previous denoised EA.

In some aspects, the computing system can feed information to other devices in the surgical environment that allows these devices to manually or automatically ameliorate or mitigate the physiological changes and improve subsequently acquired EP waveforms.

In some aspects, the computing system can obtain information from an anesthesia or blood pressure machine; and determine when changes in EP waveforms are due to anesthesia or blood pressure changes.

In some aspects, the computing system can processes EAs sequentially looking for one or more characteristics.

In some aspects, the computing system can process EA sequentially looking a change in one or more characteristics.

In some aspects, the characteristics comprise at least one of amplitude, rise time, fall time, peak duration and pre and post peak slope.

In some aspects, the computing system can alter the one or more characteristics.

In some aspects, the apparatus can include a graphical alerting system that conveys a change in EAs to a user.

In some aspects, a method of automatically improving signals received from a patient's physiological system can include stimulating a peripheral nerve with electrical pulses; recording resultant electrical waveforms (EPs) generated by the nervous system though electrodes placed over the nerve pathway; calculating an ensemble average waveform (EA) of a subset of the plurality of EPs; applying a mathematical wavelet transform to the resultant EA; attenuating noise components from the transformed EA; and applying an inverse transform to the transformed EA to generate a denoised EA, among other things.

In some aspects, the method can include calculating a change in the denoised EA relative to a previous denoised EA; and providing an alert based on the calculated change.

In some aspects, the method can include feeding information to other devices in a surgical environment thereby allowing these devices to manually or automatically identify changes between the denoised EA and a previous denoised EA.

In some aspects, the method can include feeding information to other devices in a surgical environment thereby allowing these devices to manually or automatically ameliorate or mitigate the physiological changes and improve subsequently acquired EP waveforms.

In some aspects, the method can include obtaining information from an anesthesia or blood pressure machine; and determining when changes in EP waveforms are due to anesthesia or blood pressure changes.

In some aspects, the method can include processing EAs sequentially looking for one or more characteristics.

In some aspects, the method can include processing EAs sequentially looking a change in one or more characteristics.

In some aspects, the characteristics comprise at least one of amplitude, rise time, fall time, peak duration and pre and post peak slope.

In some aspects, the method can include altering the one or more characteristics.

In some aspects, the method can include conveying a change in EAs to a user.

In some aspects, electrodes are placed at the neck or head.

In some aspects, a method of automatically improving signals received from a patient's physiological system can include delivering stimulation signals to a nerve pathway of a patient with electrical pulses via electrodes placed over the nerve pathway to generate a plurality of resultant electrical waveforms (EPs) based on a plurality of electrophysiological responses (ERs); recording the plurality of resultant EPs; generating an ensemble average waveform (EA), the generating comprising averaging a subset of the plurality of ERs; and denoising the EA, the denoising comprising applying a wavelet transform to the EA.

In some aspects, an automated evoked potential analysis system for improved monitoring, detecting and identifying changes to a patient's physiological system can include an input device, at least one processor, and at least one memory. The input device can obtain electrical potential data from the patient's physiological system after application of stimulation to a patient's nerve pathway. The at least one memory can store instructions which, when executed by the at least one data processor, result in operations comprising: causing stimulation of a nerve pathway of a patient with electrical pulses via electrodes placed over the nerve pathway to generate a plurality of resultant electrical waveforms (EPs) based on a plurality of electrophysiological responses (ERs); recording the plurality of resultant EPs; generating an ensemble average waveform (EA), the generating comprising averaging a subset of the plurality of ERs; and denoising the EA, the denoising comprising applying a wavelet transform to the EA.

Further features and advantages of the current subject matter, as well as the structure and operation of various embodiments of the invention, are described in detail below with reference to the accompanying drawings.

BRIEF DESCRIPTION OF THE DRAWINGS

The foregoing and other features and advantages of the invention will be apparent from the following, more particular description of a preferred embodiment of the invention, as illustrated in the accompanying drawings.

DETAILED DESCRIPTION

Various exemplary embodiments of the invention including preferred embodiments are discussed in detail below. While specific exemplary embodiments are discussed, it should be understood that this is done for illustration purposes only. A person skilled in the relevant art will recognize that other components and configurations can be used without parting from the spirit and scope of the invention.

Figure 1:
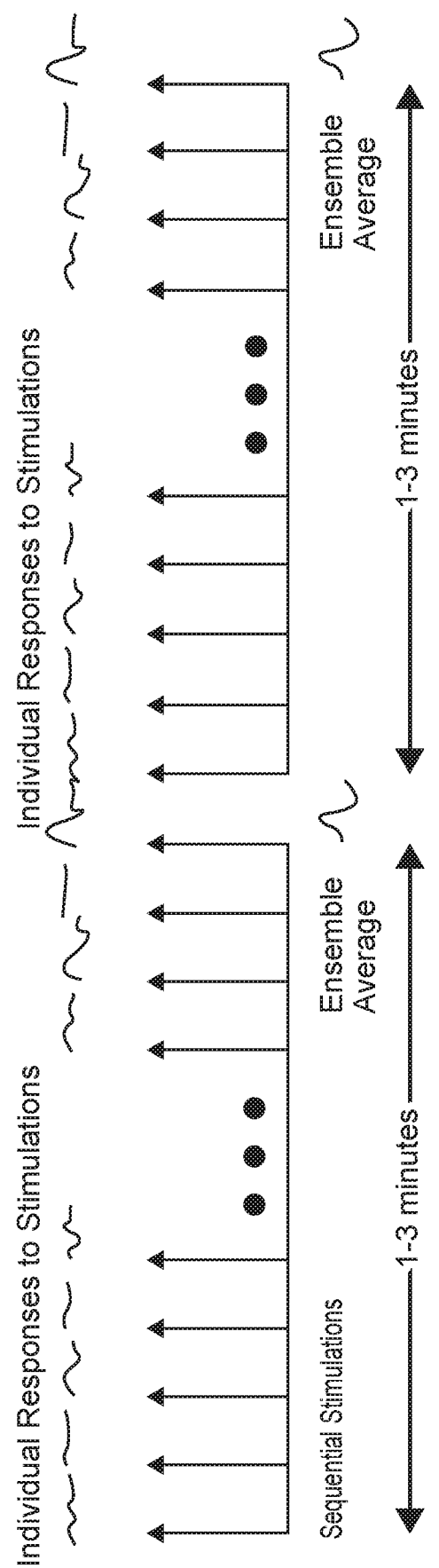
FIG. 1 illustrates a typical method of evoked potential waveform (EP) acquisition and display.

FIG. 1. illustrates a typical method in which EPs are acquired and displayed. Using this method, a series of stimulations are applied and the resultant individual waveforms are displayed either as each is acquired, or as an evolving average of the ongoing average until a final ensemble average is acquired and displayed on which to base clinical interpretation. If the user is satisfied with the average they may set that average as the 'baseline' to which all others are compared, or repeat it to confirm the presence and morphology of the waveform of interest. The whole process can then be repeated with the next series of stimulations. Comparison of that series is then made to the preceding one that is chosen to be the baseline.

Since as few as five or six noisy individual waveforms that escape filtering can cause the waveform morphology, amplitude, and latency to widely vary, applying this method in an electrically noisy environment may lead to erroneous alerting of potential, imminent injury if an automated alerting system is used. This generally requires expert interpretation of the individual waveforms that takes into account the clinical situation, expected waveform and general trend in the waveform pattern over time. In some situations, placing electrodes on the patient can cause a significant amount of noise. This can cause the recorded amplitudes to be larger or smaller. Such situations can significantly alter the averaged waveform. In some typical methods, such as described herein and/or as shown in FIG. 1, if signals are measured, such as in a high noise environment, the signal may be significantly distorted. In such typical situations, it can be difficult to differentiate between false positives and/or negatives. Noise can add a significant amount of variance in measured amplitude and/or latency. Certain portions of the body may make it more difficult to determine whether a change is due to noise or otherwise without examples of the post-processing techniques described herein. Typical systems can make it difficult to automate alerting when a change is determined due to noise or otherwise and/or differentiate from a false positive and/or negative. As described herein, implementations according to the current subject matter can help to reduce noise, such as by using post-processing techniques to minimize and/or eliminate noise in the averaged signal. Such noise may be minimized and/or eliminated, reducing and/or eliminating false positives and/or false negatives determined by the system.

An embodiment of the present invention relates to the computer signal processing and algorithms for attenuating or removing confounding artifact or similar noise, and feed the resultant signal to an automated alerting algorithm to improve recognition of changes in the underlying signals. This system may substitute for the expert analysis typically provided by the technologist and physician. The computer algorithm running in software installed on an EP machine may be used in any surgery or situation where a patient is at risk, in order to detect, alert, and ameliorate positioning effect, or any nerve injury or abnormality.

Figure 2A:
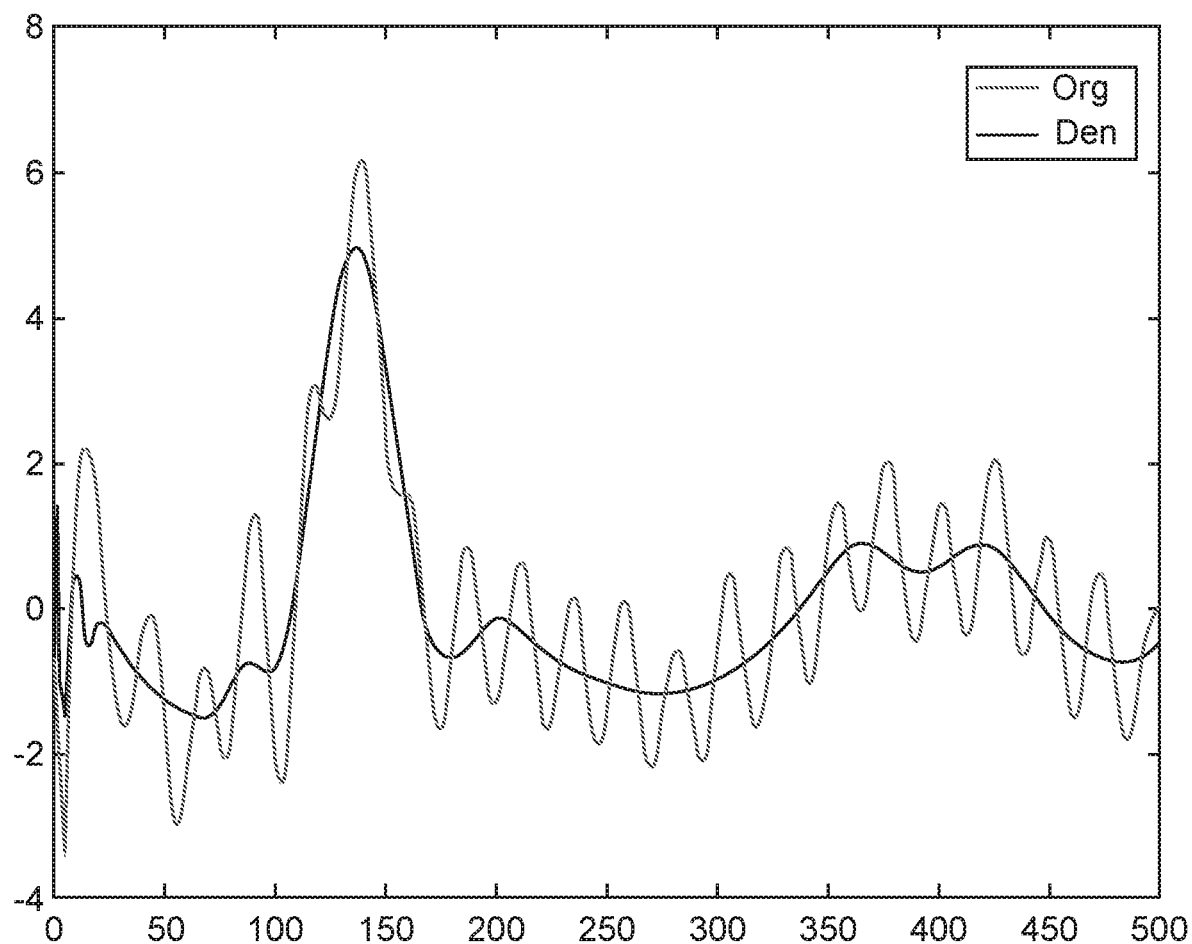
FIG. 2A illustrates a comparison of an ensemble average with and without application of a filtering technique according to implementations of the current subject matter.

FIG. 2A illustrates a comparison between a somatosensory evoked response ensemble average signal obtained with typical filtering techniques and a somatosensory evoked response ensemble average signal obtained with a denoising filter as described herein. As shown in at least FIG. 2A, the denoised signal is smoother and has reduced extraneous peaks, while still maintaining the overall morphology of the signal. The denoised signal provides better reliability of the signal and the generation of an alert resulting therefrom.

Figure 2B:
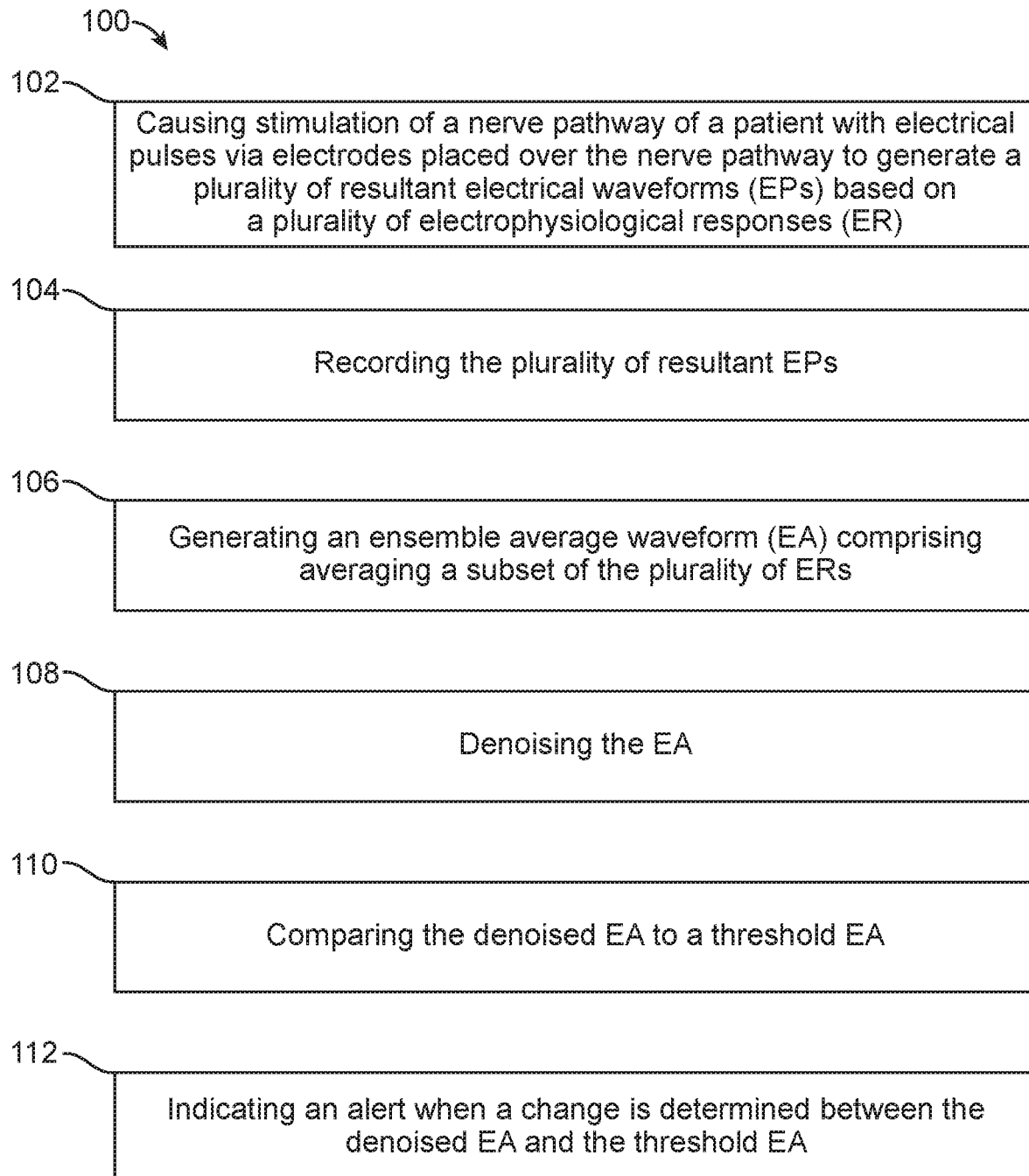
FIG. 2B illustrates an example method of improving signals according to implementations of the current subject matter.

FIG. 2B illustrates an example method 100 for automatically improving signals received from a patient's physiological system according to implementations of the current subject matter.

At step 102, the system can (e.g., automatically) cause stimulation of a nerve pathway of the patient with electrical pulses via electrodes placed over the nerve pathway. The stimulation can generate a plurality of resultant EPs from a plurality of electrophysiological responses (ERs). The plurality of resultant EPs can be recorded, for example automatically recorded, by the system at step 104.

At step 106, the system can (e.g., automatically) generate an ensemble average waveform (EA). The EA can be generated using at least a subset of the plurality of ERs. The EA waveform can be determined and/or otherwise calculated using methods described herein. For example, in some implementations, the EA can be automatically calculated from ERs using one or more averaging techniques and rejection classifiers.

At step 108, the EA can be automatically denoised. In some implementations, the denoising method can include applying (e.g., automatically applying) at least one wavelet transform, such as a mathematical wavelet transform, to the EA. As explained below, in some implementations, noise components can be attenuated from the transformed EA and/or an inverse transform can be applied to the transformed EA to generate a denoised EA.

In some implementations, the wavelet transform can include a discrete wavelet transform (DWT) and/or an inverse discrete wavelet transform (IDWT), among others. Assuming a finite length signal with a length equal to some power of 2, the transform can be computed using Mallat's algorithm.

Before and/or after the wavelet transform is applied to the EA, the EA can be decomposed, such as by automatic decomposition. For example, the system can decompose the signal in a hierarchical fashion, such as by using a series of filter banks, chosen to divide the signal power spectrum consecutively using several levels of low-pass (LP) and/or high-pass (HP) filter pairs. In some examples, each LP and HP filter pair divides the power spectrum in half. At the output of each filter, the signal can be decimated by a factor of 2, according to the Nyquist Criterion. In some implementations, the LP and HP filters can be applied to the signal in at least one iteration. For example, the initial EA can be decomposed by a pair of LP and HP filters to generate two signal bands. Each resultant signal band can then be decomposed further by a second pair of LP and HP filters to generate two signal bands for each of the signal bands. Such decomposition can result in four signal bands, etc. The hierarchical decomposition can be iterated at least five or six times. In some implementations, the hierarchical decomposition can be iterated for less than 10 times. The hierarchical decomposition can allow the filtering of high-frequency noise, for example. Such configurations can help to desirably focus on low-frequency signals. This can help to produce more accurate waveforms and/or measurements.

In some implementations, the filter coefficients of the LP and HP filters can derived from the mother wavelet. The LP coefficients are denoted as the approximation coefficients and the HP coefficients are called the detail coefficients. By assuming that the recorded, and/or EA can be represented as a series of noise-less samples, contaminated by noise: $y_{\_}(i=f(t\_i)+)n\_i$ where ni is $N(0, \sigma)$, and f(ti) are the noiseless samples.

By the orthogonal property of the mother wavelet, the wavelet coefficients can translate into wavelet coefficients also contaminated with white noise. The coefficients of the DWT may be sparse, such that a threshold can be applied to the coefficients to de-noise the signal. Applying a threshold to the coefficients performs the de-noising; if the threshold is not met, the coefficients are set to zero. The time-domain signal can then recovered by applying the IDWT.

In some implementations, the denoised EA can be compared, such as automatically compared, to a threshold EA, such as at step 110. The threshold EA can be the previously denoised EA and/or any selected previously denoised EA, and/or other EA. By comparing the denoised EA to the threshold EA, the system can determine whether any changes have occurred in the denoised EA relative to the threshold EA.

At step 112, the system can indicate (e.g., automatically) an alert when a change is determined between the denoised EA and the threshold EA. In some implementations, one or more of the denoised EAs are fed to an alerting process. The alerting process can calculate changes in one or more of amplitude, latency or morphology, among other characteristics of the waveform. In some implementations, the method may display the denoised EAs, EPs, and/or ERs, and/or use the denoised EAs, EPs, and/or ERs, for calculation in the alerting process.

According to implementations of the current subject matter, various thresholds may be used to optimize the denoising calculation. In some implementations, various known or constructed mother wavelets may be used in the de-noising calculation and calculation may be taken to 1 or more levels of decomposition. In an exemplary embodiment of the present invention scaling of the source EAs may be undertaken to optimize the results of the de-noising calculation.

Figure 3:
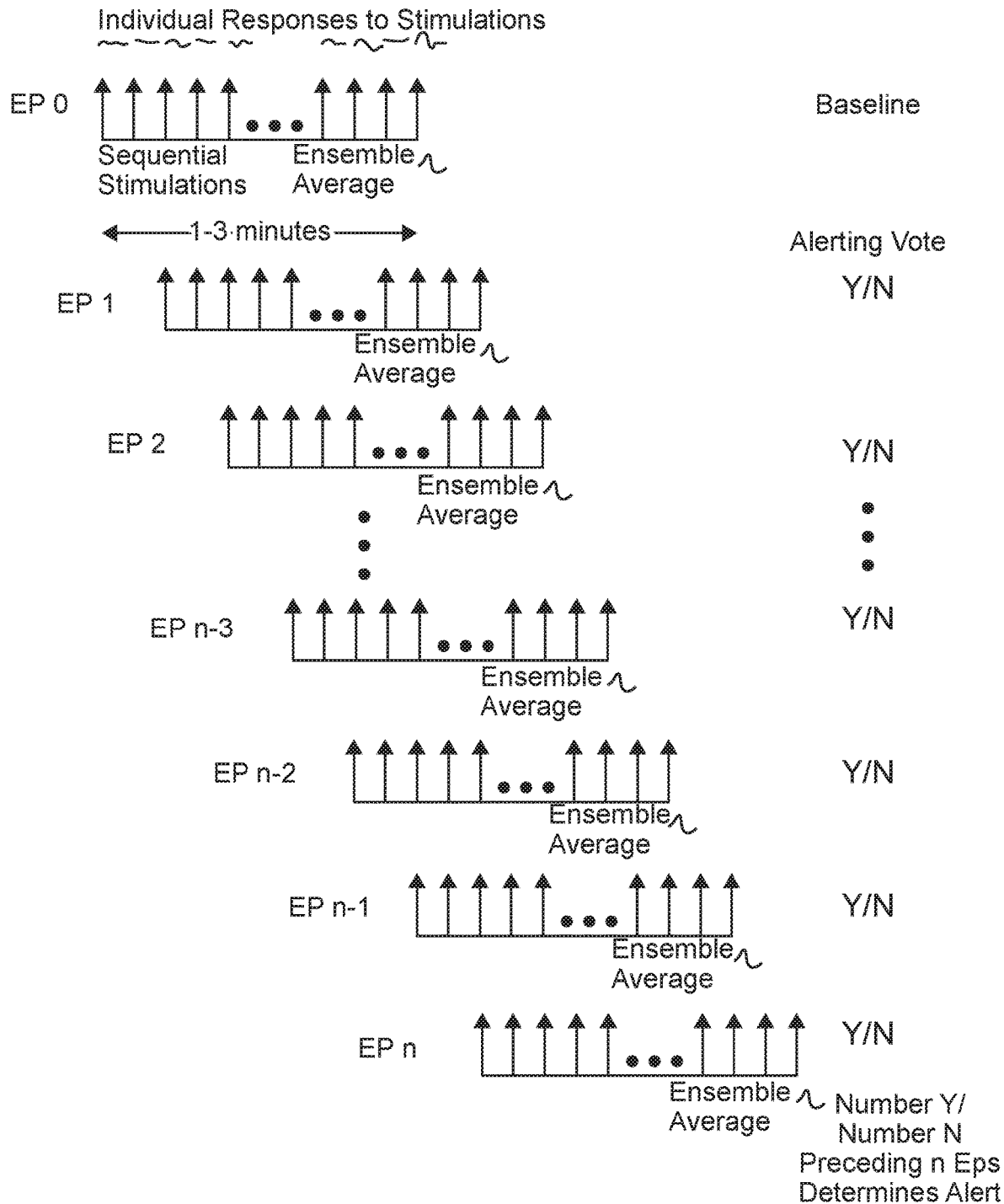
FIG. 3 illustrates a sliding window method of EP acquisition, display, and alerting, according to implementations of the current subject matter.

FIG. 3 illustrates an exemplary depiction of a sliding window of analysis and alerting using metadata from automatically calculated alerts that takes into consideration variation in noise and automatically looks back at the trend of the waveform over time, according to the present invention. This sliding window analysis and alerting process may be used in addition to, in conjunction with, before, or after the application of the method of improving signals and/or filtering described above. Examples of the sliding window analysis and alerting process is described in International Patent Application No. PCT/US2016/0030605 (published as International Publication WO2016/179191), filed May 3, 2016, entitled "SYSTEM, METHOD, AND COMPUTER ALGORITHM FOR MEASURING, DISPLAYING, AND ACCURATELY DETECTING CHANGES IN ELECTROPHYSIOLOGICAL EVOKED POTENTIALS," which is incorporated by reference herein in its entirety.

Figure 4:
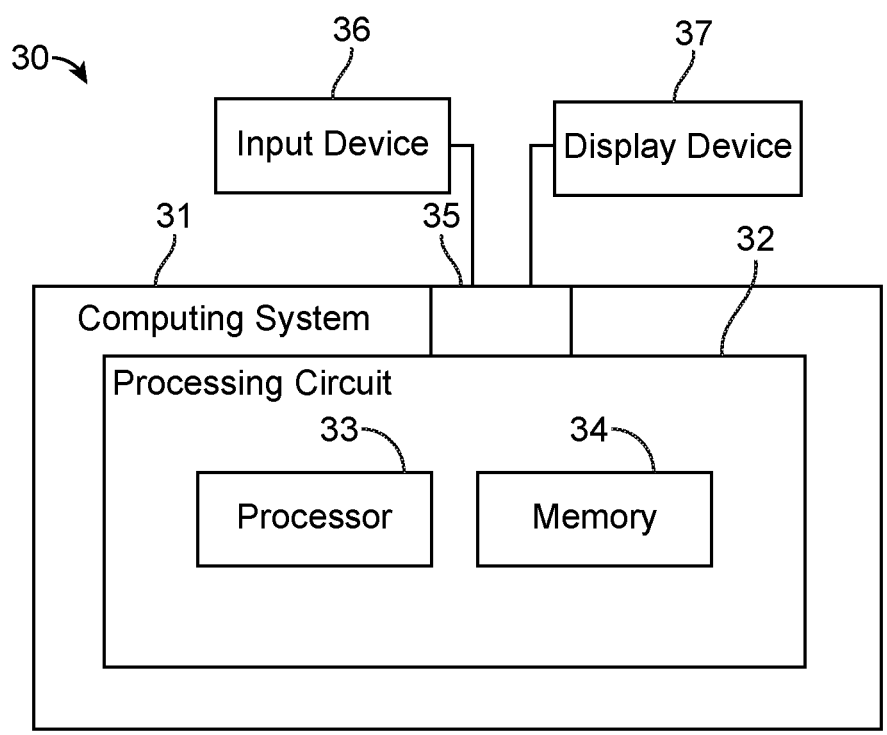
FIG. 4 is a block diagram of a model EP analysis apparatus according to implementations of the current subject matter.

Referring to FIG. 4, according to some implementations of the current subject matter, the EP analysis described above is implemented with an EP analysis apparatus 30. The EP analysis apparatus 30 includes hardware and software for operation and control of the system. According to some implementations, the EP analysis apparatus 30 includes a computing system 31, an input device 36, and a graphical alerting system, such as display device 37, among other components. The computing system comprises a processing circuit 32 having a processor 33 and memory 34. Processor 33 can be implemented as a general purpose processor, an application specific integrated circuit (ASIC), one or more field programmable gate arrays (FPGAs), a group of processing components, or other suitable electronic processing components. Memory 34 (e.g., memory, memory unit, storage device, etc.) is one or more devices (e.g., RAM, ROM, Flash-memory, hard disk storage, etc.) for storing data and/or computer code for completing or facilitating the various processes described in the present application. Memory 34 may be or include volatile memory or non-volatile memory. Memory 34 may include database components, object code components, script components, or any other type of information structure for supporting the various activities described in the present application. According to some implementations, memory 34 is communicably connected to processor 33 and includes computer code for executing one or more processes described herein. The memory 34 may contain a variety of modules, each capable of storing data and/or computer code related to specific types of functions.

Referring still to FIG. 4, the computing system 31 further includes a communication interface 35. The communication interface 35 can be or include wired or wireless interfaces (e.g., jacks, antennas, transmitters, receivers, transceivers, wire terminals, etc.) for conducting data communications with external sources via a direct connection or a network connection (e.g., an Internet connection, a LAN, WAN, or WLAN connection, etc.).

What is claimed is:

1. A medical method of automatically improving signals received from a patient's physiological system comprising:
    delivering stimulation signals to a nerve pathway of a patient with electrical pulses via electrodes placed over the nerve pathway to generate a plurality of resultant evoked potentials (EPs) based on a plurality of electrophysiological responses (ERs);
    recording the plurality of resultant EPs;
    generating an ensemble average waveform (EA), the generating comprising averaging a subset of the plurality of ERs;
    denoising the EA to generate a denoised EA comprising a denoised signal, the denoising comprising:
        decomposing, hierarchically, the EA using a series of filter banks, wherein filter coefficients of the series of filter banks used in the hierarchical decomposition are derived from a mother wavelet derived from an electrophysiological response of interest, and wherein the decomposing comprises applying a first wavelet transform;
        iterating the hierarchical decomposition of the EA, the hierarchical decomposition of the EA filtering high-frequency noise from the EA;
        applying a dynamic coefficient threshold to the filter coefficients, the dynamic coefficient threshold determined with the EA; and
        applying a second wavelet transform to the EA, the second wavelet transform comprising an inverse wavelet transform using the mother wavelet derived from the electrophysiological response of interest;
    comparing the denoised EA to a previously denoised EA;
    determining whether a change has occurred in the denoised EA relative to the previously denoised EA; and
    generating, based on the determination that the change has occurred, an alert.

2. The method of claim 1, wherein the denoising further comprises: attenuating noise components from the transformed EA by decomposing the transformed EA; and wherein the second wavelet transform comprises an inverse transform applied to the transformed EA to generate the denoised EA.

3. The method of claim 1, further comprising comparing the denoised EA to a threshold EA.

4. The method of claim 3, wherein the threshold EA includes the previously denoised EA.

5. The method of claim 3, further comprising determining a change between the denoised EA and the threshold EA.

6. The method of claim 5, further comprising indicating an alert that the change between the denoised EA and the threshold EA has occurred.

7. The method of claim 1, further comprising transmitting information to other devices in a surgical environment thereby allowing the devices to manually or automatically identify changes between the denoised EA and the previously denoised EA.

8. The method of claim 1, further comprising: obtaining information from an anesthesia or blood pressure machine; and determining when changes in EPs are due to anesthesia or blood pressure changes.

9. The method of claim 1, further comprising displaying the denoised EA on a monitor device.

10. An automated electrical waveforms (EPs) analysis system for improved monitoring, detecting and identifying changes to a patient's physiological system, wherein the system comprises:
    an input device for obtaining electrical potential data from the patient's physiological system after application of stimulation to a patient's nerve pathway;
    at least one processor; and
    at least one memory storing instructions which, when executed by the at least one processor, result in operations comprising:
        causing stimulation of a nerve pathway of a patient with electrical pulses via electrodes placed over the nerve pathway to generate a plurality of resultant electrical waveforms (EPs) based on a plurality of electrophysiological responses (ERs);
        recording the plurality of resultant EPs;
        generating an ensemble average waveform (EA), the generating comprising averaging a subset of the plurality of ERs;
        denoising the EA to generate a denoised EA comprising a denoised signal, the denoising comprising:
            decomposing, hierarchically, the EA using a series of filter banks, wherein filter coefficients of the series of filter banks used in the hierarchical decomposition are derived from a mother wavelet derived from an electrophysiological response of interest, and wherein the decomposing comprises applying a first wavelet transform;
            iterating the hierarchical decomposition of the EA, the hierarchical decomposition of the EA filtering high-frequency noise from the EA;
            applying a dynamic coefficient threshold to the filter coefficients, the dynamic coefficient threshold determined with the EA; and
            applying a second wavelet transform to the EA, the second wavelet transform comprising an inverse wavelet transform using the mother wavelet derived from the electrophysiological response of interest;
        comparing the denoised EA to a previously denoised EA;

determining whether a change has occurred in the denoised EA relative to the previously denoised EA; and generating, based on the determination that the change has occurred, an alert.

11. The system of claim 10, wherein the denoising further comprises: attenuating noise components from the transformed EA by decomposing the transformed EA; and wherein the second wavelet transform comprises an inverse transform applied to the transformed EA to generate the denoised EA.

12. The system of claim 10, wherein the operations further comprises comparing the denoised EA to a threshold EA.

13. The system of claim 12, wherein the threshold EA includes the previously denoised EA.

14. The system of claim 13, wherein the operations further comprise determining a change between the denoised EA and the threshold EA.

15. The system of claim 12, wherein the operations further comprise indicating an alert that a change between the denoised EA and the threshold EA has occurred.

16. The system of claim 10, wherein the operations further comprise transmitting information to other devices in a surgical environment thereby allowing the devices to manually or automatically identify changes between the denoised EA and the previously denoised EA.

17. The system of claim 10, wherein the operations further comprise: obtaining information from an anesthesia or blood pressure machine; and determining when changes in EPs are due to anesthesia or blood pressure changes.

* * * * *